US010467210B2

(12) United States Patent
Dwire et al.

(10) Patent No.: US 10,467,210 B2
(45) Date of Patent: Nov. 5, 2019

(54) INTERPRETING HL7 SEGMENT HIERARCHY DYNAMICALLY

(71) Applicant: Health Catalyst, Inc., Salt Lake City, UT (US)

(72) Inventors: Steven E. Dwire, Lawrenceville, GA (US); Hong Gao, Alpharetta, GA (US); Sarika Kandaprabhu, Milton, GA (US); Michael Godinez, Acworth, GA (US); Hassan Khan, Alpharetta, GA (US)

(73) Assignee: Health Catalyst, Inc., Salt Lake City, UT (US)

( * ) Notice: Subject to any disclaimer, the term of this patent is extended or adjusted under 35 U.S.C. 154(b) by 199 days.

(21) Appl. No.: 15/471,908

(22) Filed: Mar. 28, 2017

(65) Prior Publication Data

US 2017/0277732 A1 Sep. 28, 2017

Related U.S. Application Data

(60) Provisional application No. 62/314,051, filed on Mar. 28, 2016.

(51) Int. Cl.
*G06F 16/30* (2019.01)
*G06F 16/22* (2019.01)
(Continued)

(52) U.S. Cl.
CPC .......... *G06F 16/22* (2019.01); *G06F 17/2247* (2013.01); *G06F 17/2705* (2013.01); *G06F 17/2785* (2013.01); *G06F 19/3418* (2013.01)

(58) Field of Classification Search
None
See application file for complete search history.

(56) References Cited

U.S. PATENT DOCUMENTS

| | | | | |
|---|---|---|---|---|
| 7,346,889 B1 * | 3/2008 | Semenov | G06F 8/51 717/106 |
| 2006/0075396 A1 * | 4/2006 | Surasinghe | G06F 8/70 717/168 |

(Continued)

OTHER PUBLICATIONS

HAPI Project, "HAPI—The Open Source HL7 API for Java," May 12, 2014 (available at: http://hl7api.sourceforge.net/index.html).

(Continued)

*Primary Examiner* — Tarek Chbouki
(74) *Attorney, Agent, or Firm* — Patent Law Works LLP

(57) ABSTRACT

Embodiments of the disclosure provide a method and system of interpreting HL7 segments of an HL7 message. The method includes: electronically obtaining and interpreting a grammar definition to determine a prescribed hierarchy of HL7 segment definitions; creating a resulting segment hierarchy data structure, the resulting segment hierarchy data structure comprising a top segment; performing steps: (a) obtaining an HL7 segment from a plurality of HL7 segments in the HL7 message, (b) determining a parent-child relationship for the HL7 segment, and (c) adding the HL7 segment to the resulting segment hierarchy data structure; and, continuing to perform steps (a), (b), and (c) on remaining HL7 segments of the plurality of HL7 segments until all HL7 segments of the HL7 message have been added to the resulting segment hierarchy data structure.

20 Claims, 6 Drawing Sheets

(51) Int. Cl.

| | |
|---|---|
| ***G06F 17/27*** | (2006.01) |
| ***G06F 17/22*** | (2006.01) |
| ***G06F 19/00*** | (2018.01) |

(56) References Cited

U.S. PATENT DOCUMENTS

2006/0161840 A1* 7/2006 Cohen ................. G06F 17/2264 715/234
2007/0044069 A1* 2/2007 Doucette ................... G06F 8/30 717/106
2008/0270438 A1* 10/2008 Aronson ................ G16H 10/40
2011/0252310 A1* 10/2011 Rahaman ............ G06F 17/2211 715/255
2012/0084074 A1* 4/2012 Chronister ............ G06F 16/353 704/9
2012/0323863 A1* 12/2012 Dove ...................... G06F 16/24 707/692

OTHER PUBLICATIONS

Mirth Connect, "User Guide," Oct. 16, 2015 (available at: http://www.mirthcorp.com/community/wiki/display/mirth/User+Guide).

Oracle, "Class StringTokenizer," Java SE 7, Jul. 7, 2011 (available at: http://docs.oracle.com/javase/7/docs/api/java/util/StringTokenizer.html#nextToken)).

Williams, Michael J., "Java Garbage Collection Basics," Mar. 12, 2015 (available at: https://web.archive.org/web/20150312191945/http://www.oracle.com/webfolder/technetwork/tutorials/obe/java/gc01/index.html).

Panwar, Abhijeet, "How String object is garbage collected in Java?" StackOverflow.com, Jul. 12, 2014 (available at: http://stackoverflow.com/questions/24711100/how-string-object-is-garbage-collected-in-java).

Corepoint Health, "HL7 ADT-Admit Discharge Transfer," Nov. 16, 2015 (available at: https://www.corepointhealth.com/resource-center/h17-resources/h17-adt).

Kim, et al. "Integration of IEEE 1451 and HL7 Exchanging Information for Patients' Sensor Data," *Journal of Medical Systems*, vol. 34, pp. 1033-1041 (Jun. 17, 2009).

Health Level Seven International, "About HL7," Nov. 16, 2015 (available at: http://www.h17.org/about/index.cfm?ref=common).

Balachandran, Mohan, "HL7 201—The Admission, Discharge, Transfer (ADT) Message," 2015 Healthcare Innovation Report: 4 Big Ideas (Feb. 15, 2014).

Health Level Seven International, "HL7 Version 2.5.1 Implementation Guide: Birth and Fetal Death Reporting, Release 1—US Realm; DSTU Release 1.1," Feb. 2015.

Health Level Seven International, "HL7 Version 2.5.1—Chapter 2: Control" Apr. 2007.

* cited by examiner

Sample grammar (For ORU messages)

```
*MSH < *PID < PD1 NTE NK1 *PV1 < PV2 >> ORC < *OBR < NTE *OBX < NTE > *SPM < OBX >>>
```

Segment Definitions created

The following structure is created by interpreting the above grammar using the logic in the first flowchart. Each bullet is a SegmentDefinition object. Sub-bullets represent members of the ordered collection of child segment definitions:

- {name = "MSH", required = true}
  - {name = "PID", required = true}
    - {name = "PD1"}
    - {name = "NTE"}
    - {name = "NK1"}
    - {name = "PV1", required=true}
      - {name = "PV2"}
  - {name = "ORC", required = false}
    - {name = "OBR", required = true}
      - {name = "NTE"}
      - {name = "OBX", required = true}
        - {name = "NTE"}
      - {name = "SPM", required = true}
        - {name = "OBX"}

FIG. 1A

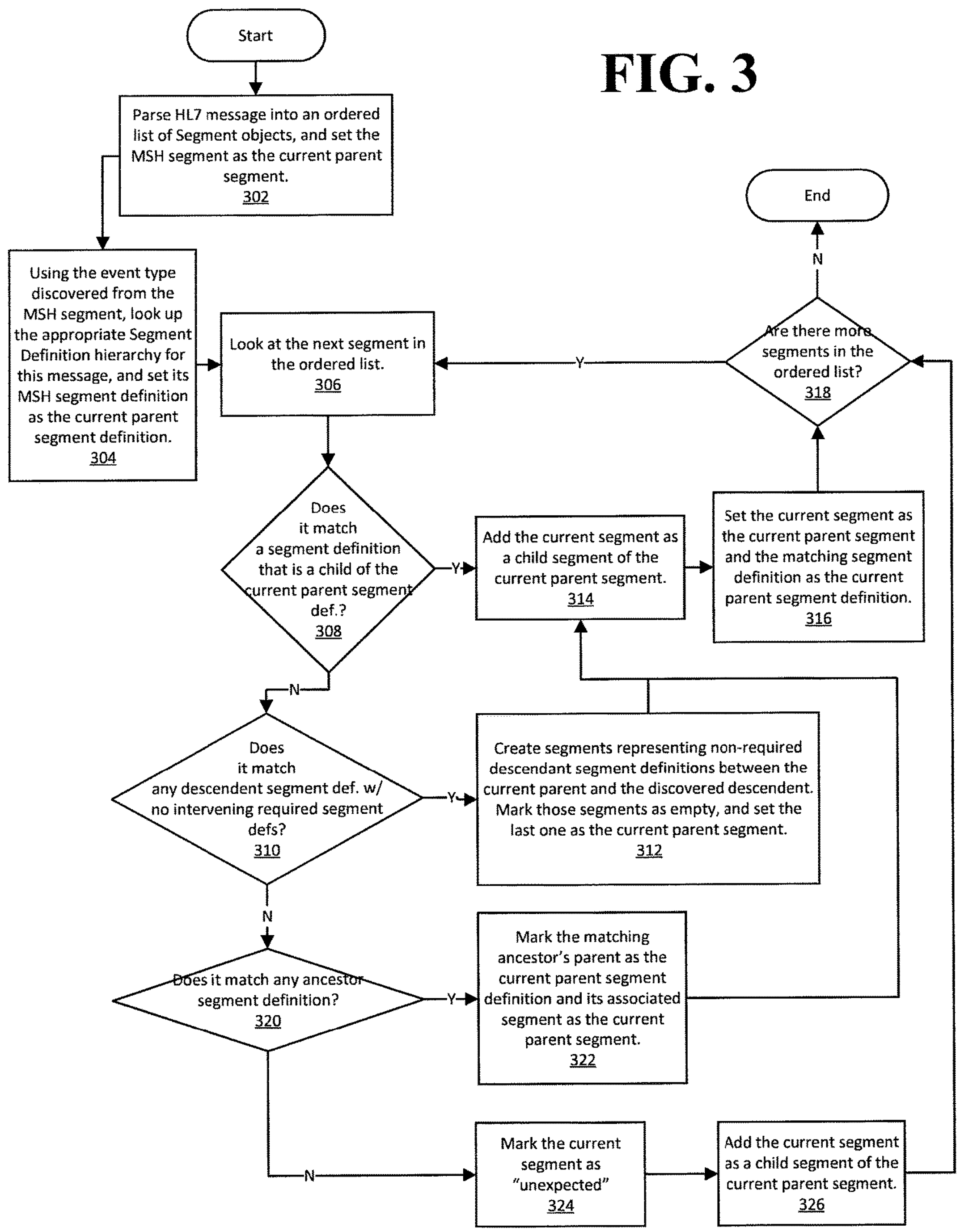

FIG. 3
Start
Parse HL7 message into an ordered list of Segment objects, and set the MSH segment as the current parent segment.
302
Using the event type discovered from the MSH segment, look up the appropriate Segment Definition hierarchy for this message, and set its MSH segment definition as the current parent segment definition.
304
Look at the next segment in the ordered list.
306
Does it match a segment definition that is a child of the current parent segment def.?
308
Add the current segment as a child segment of the current parent segment.
314
Set the current segment as the current parent segment and the matching segment definition as the current parent segment definition.
316
Are there more segments in the ordered list?
318
End
Does it match any descendent segment def. w/ no intervening required segment defs?
310
Create segments representing non-required descendant segment definitions between the current parent and the discovered descendent. Mark those segments as empty, and set the last one as the current parent segment.
312
Does it match any ancestor segment definition?
320
Mark the matching ancestor's parent as the current parent segment definition and its associated segment as the current parent segment.
322
Mark the current segment as "unexpected"
324
Add the current segment as a child segment of the current parent segment.
326
Y
N

Sample HL7 Message Segment Sequence

| Sample A | Sample B |
|---|---|
| MSH\|... | MSH\|... |
| PID\|... | PID\|... |
| ORC\|... | OBR\|... |
| OBR\|... | NTE\|... |
| OBX\|... | OBX\|... |
| Z01\|... | OBX\|... |
| NTE\|... | OBR\|... |
| | Z01\|... |
| | OBX\|... |
| | OBX\|... |
| | NTE\|... |

Resulting Segment Hierarchy Structures

The following structures are created by applying the logic from the second flowchart, using the Segment Definitions created by the first part of this document and the sample messages described in the previous section

Sample A

- {name = "MSH"}
  - {name = "PID"}
  - {name = "ORC"}
    - {name = "OBR"}
      - {name = "OBX"}
        - {name = "Z01", unexpected=true}
        - {name = "NTE"}

Sample B

- {name = "MSH"}
  - {name = "PID"}
  - {name = "ORC", empty=true}
    - {name = "OBR"}
      - {name = "NTE"}
      - {name = "OBX"}
      - {name = "OBX"}
    - {name = "OBR"}
      - {name = "Z01", unexpected=true}
      - {name = "OBX"}
      - {name = "OBX"}
        - {name = "NTE"}

FIG. 4

INTERPRETING HL7 SEGMENT HIERARCHY DYNAMICALLY

CROSS-REFERENCE TO RELATED APPLICATIONS

This application claims the benefit of U.S. Provisional Application No. 62/314,051, filed on Mar. 28, 2016, which is hereby incorporated by reference in its entirety.

BACKGROUND

Health Level-7 or HL7 refers to international standards for transfer of data between software applications used by various healthcare providers. These different providers, departments, or organizations may operate disparate computer systems to process, share, and organize the different data. It is desirable that these computer systems interface with each other allowing transfer of data between the different computing systems. HL7 is a standard that enables such communication between the computer systems. As technology evolves and more types of information need to be stored or new links need to be made in already stored data, the HL7 standard is updated to reflect the new requirements.

HL7 messages describe healthcare events in a hierarchical manner, with a single message composed of multiple segments. Each segment is composed of multiple fields. Each field may have multiple repetitions. Each repetition may have multiple components, and each component may have multiple subcomponents. Changes to the HL7 standard may disrupt computing systems working with older versions of the standard, rendering those systems incompatible with the new standard.

SUMMARY

One embodiment of the disclosure provides a method for interpreting HL7 segments of an HL7 message. The method includes: electronically obtaining and interpreting a grammar definition to determine a prescribed hierarchy of HL7 segment definitions; creating a resulting segment hierarchy data structure, the resulting segment hierarchy data structure comprising a top segment; performing steps: (a) obtaining an HL7 segment from a plurality of HL7 segments in the HL7 message, (b) determining a parent-child relationship for the HL7 segment, and (c) adding the HL7 segment to the resulting segment hierarchy data structure; and, continuing to perform steps (a), (b), and (c) on remaining HL7 segments of the plurality of HL7 segments until all HL7 segments of the HL7 message have been added to the resulting segment hierarchy data structure.

Another embodiment of the disclosure provides a computing device for interpreting HL7 segments of an HL7 message, the computing device comprising a processor and a memory with instructions stored thereon, such that when the processor executes the instructions, the device is configured to: electronically obtain and interpret a grammar definition to determine a prescribed hierarchy of HL7 segment definitions; create a resulting segment hierarchy data structure, the resulting segment hierarchy data structure comprising a top segment; perform steps: (a) obtaining an HL7 segment from a plurality of HL7 segments in the HL7 message, (b) determining a parent-child relationship for the HL7 segment, and, (c) adding the HL7 segment to the resulting segment hierarchy data structure; and, continue performing steps (a), (b), and (c) on remaining HL7 segments of the plurality of HL7 segments until all HL7 segments of the HL7 message have been added to the resulting segment hierarchy data structure.

Yet another embodiment of the disclosure provides a non-transitory computer readable medium for interpreting HL7 segments of an HL7 message, the non-transitory computer readable medium containing program instructions that causes a computer to perform the method comprising: electronically obtaining and interpreting a grammar definition to determine a prescribed hierarchy of HL7 segment definitions; creating a resulting segment hierarchy data structure, the resulting segment hierarchy data structure comprising a top segment; performing steps: (a) obtaining an HL7 segment from a plurality of HL7 segments in the HL7 message, (b) determining a parent-child relationship for the HL7 segment, and (c) adding the HL7 segment to the resulting segment hierarchy data structure; and, continuing to perform steps (a), (b), and (c) on remaining HL7 segments of the plurality of HL7 segments until all HL7 segments of the HL7 message have been added to the resulting segment hierarchy data structure.

BRIEF DESCRIPTION OF THE DRAWINGS

FIG. 1A provides a sample HL7 grammar structure and the grammar structure's interpretation;

FIG. 3 is an example flow diagram to interpret an HL7 message in accordance with some embodiments of the disclosure;

FIG. 4 is an example showing results on sample HL7 messages after interpreting the HL7 messages in accordance with some embodiments of the disclosure.

DETAILED DESCRIPTION

Figure 1B:
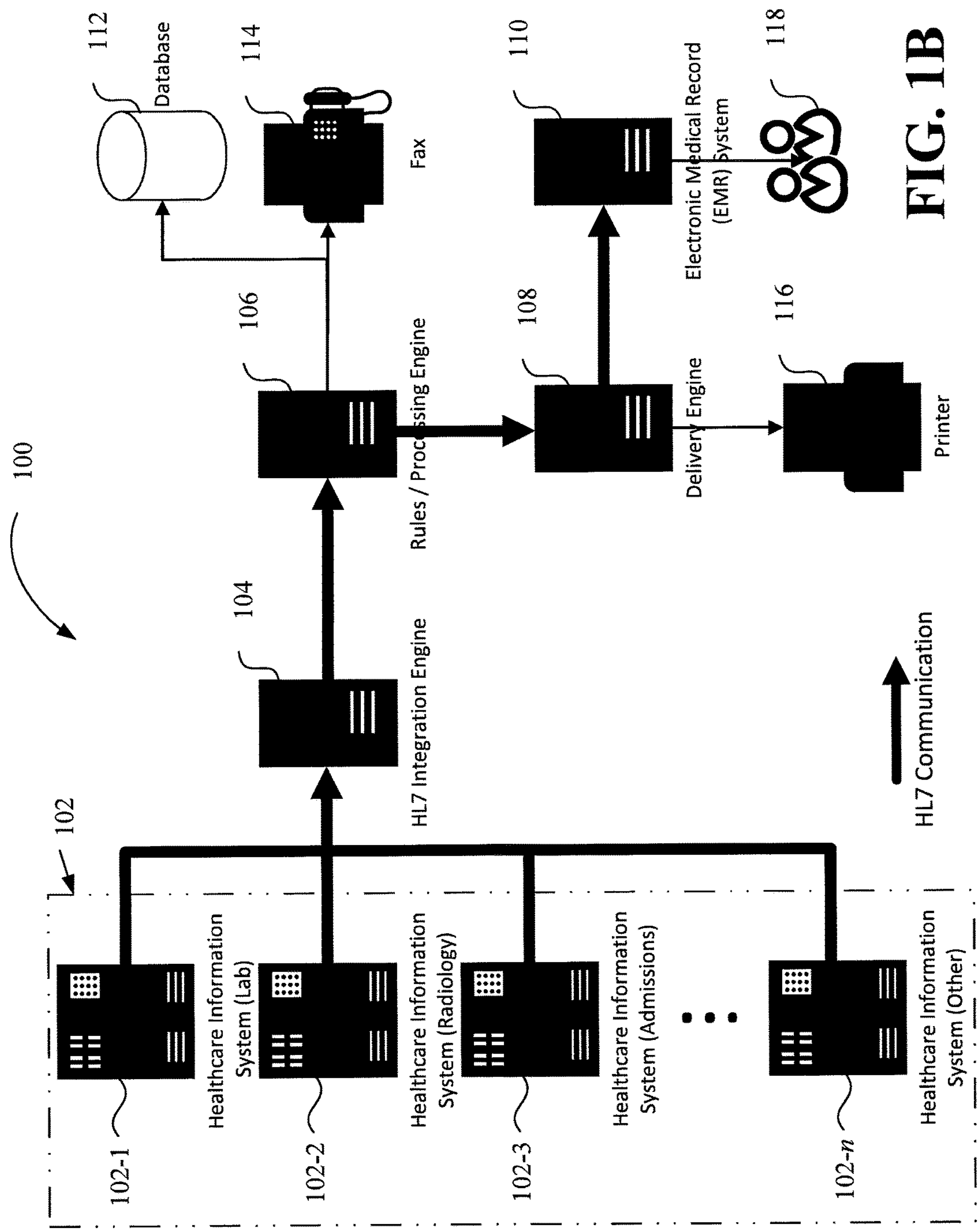
FIG. 1B provides an example of a schematic illustrating an overview of a system for the flow of HL7 communication.

Embodiments of the disclosure provide a method and system to interpret HL7 messages. Healthcare information is often communicated between computer systems from different vendors using a loosely-defined industry-standard format called HL7. HL7 defines the general structure and semantics of communication, but often leaves details to the discretion of different vendors. HL7 messages describe healthcare events in a hierarchical manner, with a single message composed of multiple segments. Each segment is composed of multiple fields. Each field may have zero or more repetitions. Each repetition may have multiple components, and each component may have multiple subcomponents.

In addition to this explicit hierarchy is an implied hierarchy of relationships between various segments of an HL7 message. For example, a segment representing a single observation from a blood sample can be considered to "belong to" a segment representing the ordered blood test that includes that observation. The knowledge of these relationships between segments cannot be derived from the structure of the message itself, but must be inferred from external documentation, published by Health Level Seven® International, about the specific healthcare events. The expected segments and the relationships between them are usually different for different kinds of healthcare events. For example, the segments reporting information about a patient's transfer from one room to another will be different from the segments reporting information about the intravenous admission of a prescription drug during the hospital stay. Software libraries are currently available to allow the interpretation and manipulation of the hierarchy of information in HL7 format, but the existing approaches take the knowledge of the relationships between segments from the documentation and compile them into separate implementation classes for each kind of segment defined in the documentation. When Health Level Seven® International publishes a new version of the HL7 standard, these existing libraries must have additional classes created and compiled, and a new version of the software library must be acquired, installed, and integrated into a software client in order to support the new or changed relationships. This process is resource intensive and undesirable.

Embodiments of the disclosure allow a software client to describe the relationships between segments dynamically at runtime using a simple grammar. Therefore, when Health Level Seven® International publishes a new version of the HL7 standard defining new or changed relationships between segments, certain embodiments of the disclosure can learn of these new relationships from the software client—without requiring new code to be written or added in order to track those relationships.

FIG. 1A provides an example of an HL7 grammar. The asterisk "*" is used to denote a segment whose presence is required in order to interpret subsequent segments as members of that segment's hierarchy of descendants. The less than symbol "<" is used to signify stepping into the hierarchy, i.e., signify a child or children of the item that came before the symbol. The greater than symbol ">" is used to signify stepping out of the hierarchy, i.e., signify a move to a parent level of the item that came before the symbol. In certain embodiments, multiple greater than symbols may follow one another to denote moving up multiple parent levels. For example, in the sample grammar shown in FIG. 1A, MSH and PID are required to properly interpret subsequent segments as their segments' hierarchy members, with PID being a child of MSH. MSH and PID are known identifiers in HL7, and FIG. 1A provides other HL7 identifiers as well, i.e., PD1, NTE, NK1, PV1, PV2, ORC, OBR, OBX, and SPM. Referring back to the implied hierarchy in FIG. 1A, under PID are four children, PD1, NTE, NK1, and PV1. Only PV1 out of the four children is required to properly interpret PV2 as a child of PV1. Two greater than symbols follow PV2, which suggests that ORC is at the same level as PID, thus ORC is a child of MSH. Using the same logic, the rest of the grammar is read. When a software client reads the sample grammar file, the interpretation of the grammar file is as presented in the bulleted format provided in FIG. 1A. The bulleted format shows which values are required and relates children to parents. In certain embodiments, the required fields are identified, in some embodiments, the non-required fields are identified, and in other embodiments like those of FIG. 1A, both required and non-required fields are identified. For simplicity in explanation, a grammar file is used as example, but as previously mentioned the grammar definition may be provided as a string literal held in the software client or may be further provided as strings in a configuration.

FIG. 1B is a schematic illustrating an overview of an example system 100 for the flow of HL7 communication. The Healthcare Information Systems 102-1 to **102-*n* represent different computing environments that may receive and send HL7 messages. In the current embodiment, HL7 Integration Engine 104 receives HL7 messages from the multiple Healthcare Information Systems 102. For simplicity in description, reference number 102 is used herein to refer to at least one of the Healthcare Information Systems 102-1 to 102-*n*. The HL7 Integration Engine 104 may send HL7 messages to the Rules/Processing Engine 106. In turn, the Rules/Processing Engine 106 may send HL7 messages to the Delivery Engine 108, which in turn may send HL7 messages to the Electronic Medical Record (EMR) System 110. Health Information Systems 102 are each represented with a mainframe computer symbol, and the HL7 Integration Engine 104, Rules/Processing Engine 106, Delivery Engine 108, and EMR 110 are represented with a server symbol. Each of the mainframes and servers are computer devices with non-transitory computer readable medium. In some implementations, these different computing systems may comprise multiple computer devices networked to perform as a single unit, i.e., a server symbol in FIG. 1B may represent multiple servers linked to realize a prescribed functionality. The example system 100 may also include devices not compatible with HL7, for example, a fax machine 114, a printer 116, etc. In some instances, the different computing devices are coupled to one or more databases. In FIG. 1B, the Rules/Processing Engine 106 is connected to Database 112. The mainframes and servers represented in FIG. 1B may receive, manipulate, and send HL7 messages. Thus, embodiments of the disclosure may be applied at any healthcare computing device in the architecture representation of FIG. 1**B for processing HL7 messages.

Figure 2:
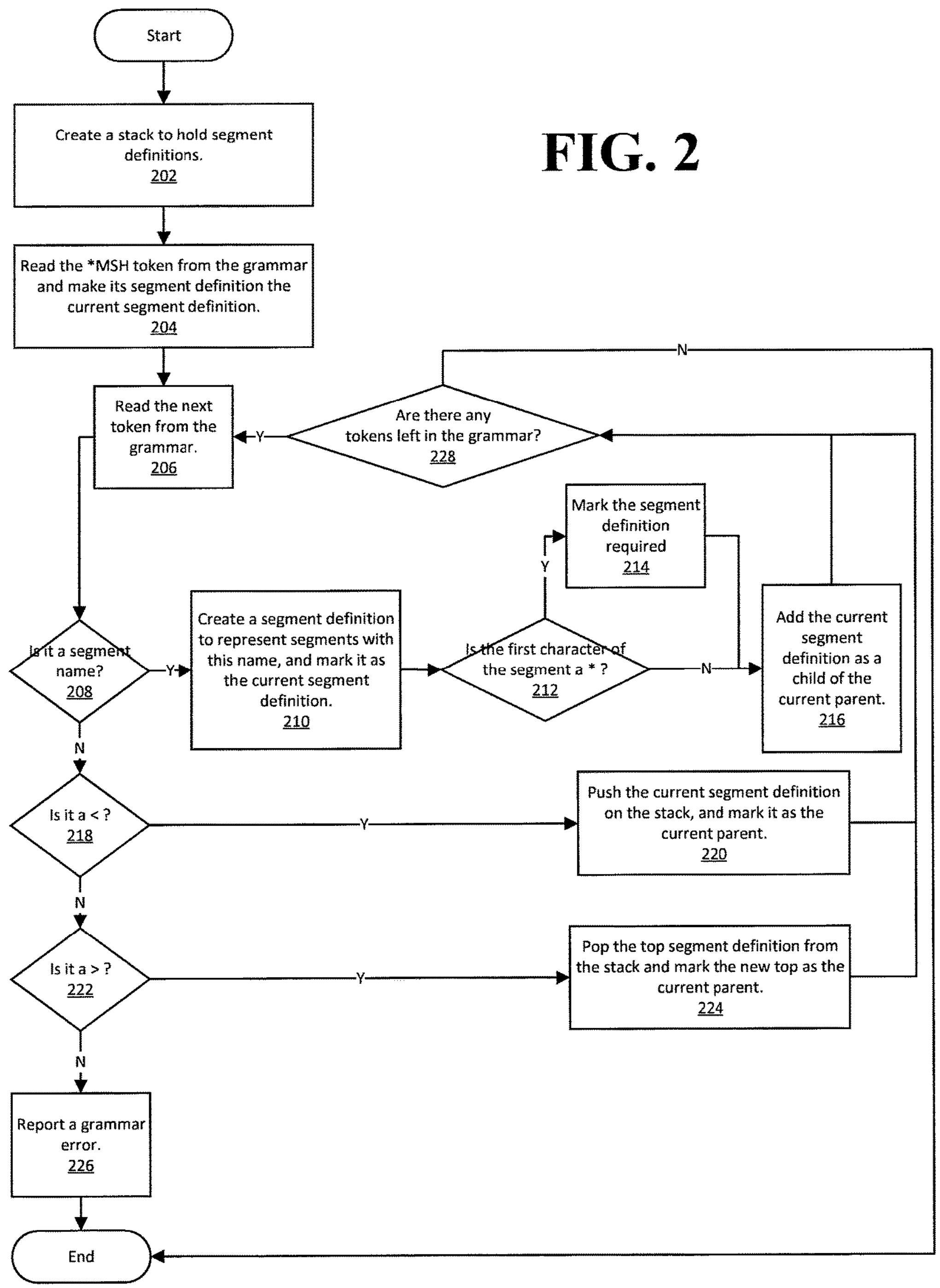
FIG. 2 is an example flow diagram to interpret a grammar input in accordance with some embodiments of the disclosure.

FIG. 2 provides an example flow diagram to interpret a grammar file, in accordance with some embodiments of the disclosure. After a change in HL7 segment relationships, instead of writing new code to interpret HL7 messages, a grammar file as provided in FIG. 1A may be written for a software client, for example, a software client running on the Rules/Processing Engine 106. The software client, upon receiving the grammar file, then utilizes an HL7 interpreter according to some embodiments of the disclosure to process the grammar file. In an embodiment, the HL7 interpreter is a software also running on the Rules/Processing Engine 106. The HL7 interpreter, after receiving the grammar from the software client, would then use the process in FIG. 2 to understand the inherent relationships within the new HL7 structure. When interpreting a grammar file, at Step 202, the HL7 interpreter on the Rules/Processing Engine 106 creates a stack to hold segment definitions. A stack data structure is used to hold a transient model of former parenthood for segment definitions during grammar parsing. Using the example from FIG. 1A, HL7 messages usually begin with an MSH segment, where an MSH segment serves as a header for an HL7 message. Thus at Step 204, the MSH token is read from the grammar file and the current segment definition is attributed to the MSH segment. The flow diagram embodiment provided in FIG. 2 uses a stack to keep track of the current parent within the hierarchy implied in the grammar file. Other data structures may be used to track the current parent. For example, an array or a linked list data structure may be utilized.

At Step 206, the HL7 interpreter on the Rules/Processing Engine 106 reads the next token from the grammar file. At Step 208, the token is compared to see whether it is a segment name. If the token is a segment name, then at Step 210, a segment definition is created to represent the segment, and the segment is marked as a current segment. Steps 212 and 214 are used to check to see whether the first character of the segment is an asterisk in order to mark the segment as required. At Step 216, the segment is added as a child of the current parent. After adding as a child, at Step 228, the HL7 interpreter checks whether there are any more tokens left in the grammar. If there are, then the next token is read at Step 206, and if not, then the process ends.

After reading the next token, at Step 208, if the token is not a segment name, then the HL7 interpreter on the Rules/Processing Engine 106 utilizes Step 218 and Step 222 to determine whether or not the token is a less than symbol or a greater than symbol, respectively. Step 220 is performed for a less than symbol, and Step 224 is performed for a greater than symbol. At Step 220, the HL7 interpreter on the Rules/Processing Engine 106 pushes the current segment definition to the stack and marks the token as the current parent. At Step 224, the HL7 interpreter on the Rules/Processing Engine 106 pops the top segment definition from the stack and marks the new top segment as the current parent. Step 226 is provided as a failsafe in case the grammar file is corrupted or not in a proper format, then the HL7 interpreter may return an error to the software client, terminating the process. The asterisk symbol, the greater than symbol, and the less than symbol are used to indicate a required segment, stepping out of a hierarchy, and stepping into the hierarchy, respectively. Other symbols may be used in the grammar for these purposes, and the use of other symbols for these purposes are within the scope of the disclosure. The software client interacting with the HL7 interpreter on the Rules/Processing Engine 106 is used as an example, but it is understood that any computing device with a processor and memory capable of processing HL7 messages may perform the steps in FIG. 2 utilizing an HL7 interpreter according to various embodiments of the disclosure.

The processing in FIG. 2 occurs while dynamically interpreting a grammar string provided by the software client. Thus, embodiments of the disclosure create a parent/child relationship between segment definitions. This parent/child relationship is then associated with a message event type or collection of message event types. The resulting relationship deciphered in FIG. 2 is stored in a non-transitory computer readable medium used to interpret and parse HL7 messages. The process of FIG. 2 results in a prescribed hierarchy of segment definitions. When an HL7 message is received, FIG. 3 provides an example flow diagram, performed by a computing device, that may be used to construct the hierarchy of the actual segments from the incoming HL7 message. The flow diagram in FIG. 3 is constructed from the perspective that the entire HL7 message is received. In other embodiments, some modifications to the flow diagram may be made to accommodate interpreting each segment of the HL7 message as it is received instead of waiting to receive the entire collection of segments in the HL7 message.

When the software client on the Rules/Processing Engine 106 receives an HL7 message, it delivers that HL7 message to the HL7 interpreter on the Rules/Processing Engine 106. At Step 302, the HL7 interpreter parses the HL7 message into an ordered list of segment objects, and in the sample HL7 message of FIG. 1 where MSH is the first segment, the MSH segment is set as the current parent segment. An MSH segment includes several fields, for example, an event type field. An example of an event type may be ADT^A08 or ORU^R01. At Step 304, using event type discovered from the MSH segment, the appropriate segment definition hierarchy (created by a process similar to FIG. 2) for the HL7 message is retrieved and its MSH segment definition is set as the current parent segment definition. MSH segment is the top segment in the hierarchy.

At Step 306, the HL7 interpreter selects the next segment in the ordered list of segments. At Step 308, Step 310, and Step 320, the HL7 interpreter compares the selected segment with known segment definitions. Segment definitions are known if these segments are defined in the grammar definitions or present in the segment definition hierarchy. If the segment at Step 306 conforms to a child of the current parent segment, then no change needs to occur to the current parent segment. If the segment at Step 306 conforms to a descendant segment with no intervening required segment definitions (Step 310), at Step 312, segments representing non-required descendant segment definitions are created between the current parent and the discovered descendant. The non-required segments created are marked as empty, and the last non-required segment created is marked as the current parent segment. The created segments not in the original message may be called "ghost segments." Instead, if the segment at Step 306 conforms to an ancestor segment (Step 320), at Step 322, the ancestor's parent is marked as the current parent segment definition and its associated segment is marked as the current parent segment. After determining the relationship between the segment of Step 306 and the current parent segment and updating the current parent segment if necessary, at Step 314, the HL7 interpreter adds the current segment as a child segment of the current parent segment.

At Step 316, the current segment is set as the current parent segment and the matching segment definition is set as the current parent segment definition. At Step 318, a check is performed to see if more segments are in the ordered list of segments. If more segments exist, then the process continues with Step 306, and if not, the process ends.

In the case where relationship between the segment at Step 306 and the current parent segment is not identified, then at Step 324, the current segment is marked as "unexpected," and at Step 326, the current segment is added as a child segment of the current parent segment. The "unexpected" marking serves as a segment definition since the segment at Step 306 does not exist in the segment definition hierarchy. In the process provided in FIG. 3, an HL7 message is received and a resulting segment hierarchy data structure is provided for the HL7 message.

Embodiments of the disclosure allow the navigation of two separate hierarchies simultaneously. The first hierarchy is the hierarchy of segment definitions—created by the one-time parsing of the grammar string, for example, using the process of FIG. 2. The second hierarchy is the hierarchy of actual segments—created by the parsing of each incoming HL7 message. Thus, the "current parent segment definition" as previously used refers to the object representing the point in the grammar definition hierarchy that one would expect to find the "current parent segment." The "current parent segment" represents data from the incoming HL7 message. The hierarchy of segment definitions is created once while the hierarchy of actual segments is created separately for each HL7 message to represent its unique content. For example, FIG. 1 shows the single hierarchy of segment definitions obtained from a grammar definition, while FIG. 4 shows two possible hierarchies of actual segments representing two different HL7 messages.

In FIG. 4, two sample HL7 messages are provided. Sample A contains seven (7) segment sequences while Sample B contains eleven (11) segment sequences. Using the grammar structure and the resulting segment definition hierarchy provided in FIG. 1A and applying the process provided in FIG. 3 to the two samples, the resultant hierarchy structures of actual segments of each sample are provided.

In FIG. 4, PID or ORC are direct descendants of MSH as provided in the grammar definition. Also, the grammar definition does not have a segment Z01, so a property identifying this segment as unexpected is set as "true." Using the same procedure, a similar result may be obtained for Sample B. The hierarchy created for Sample B illustrates the creation of a "ghost segment" ORC where a property identifying this segment as empty is set as "true." Sample B as provided does not contain an ORC segment, but when creating its hierarchy, OBR segment is encountered, and since ORC is not a required segment, a ghost ORC segment is created as a parent for the OBR segment.

Figure 5:
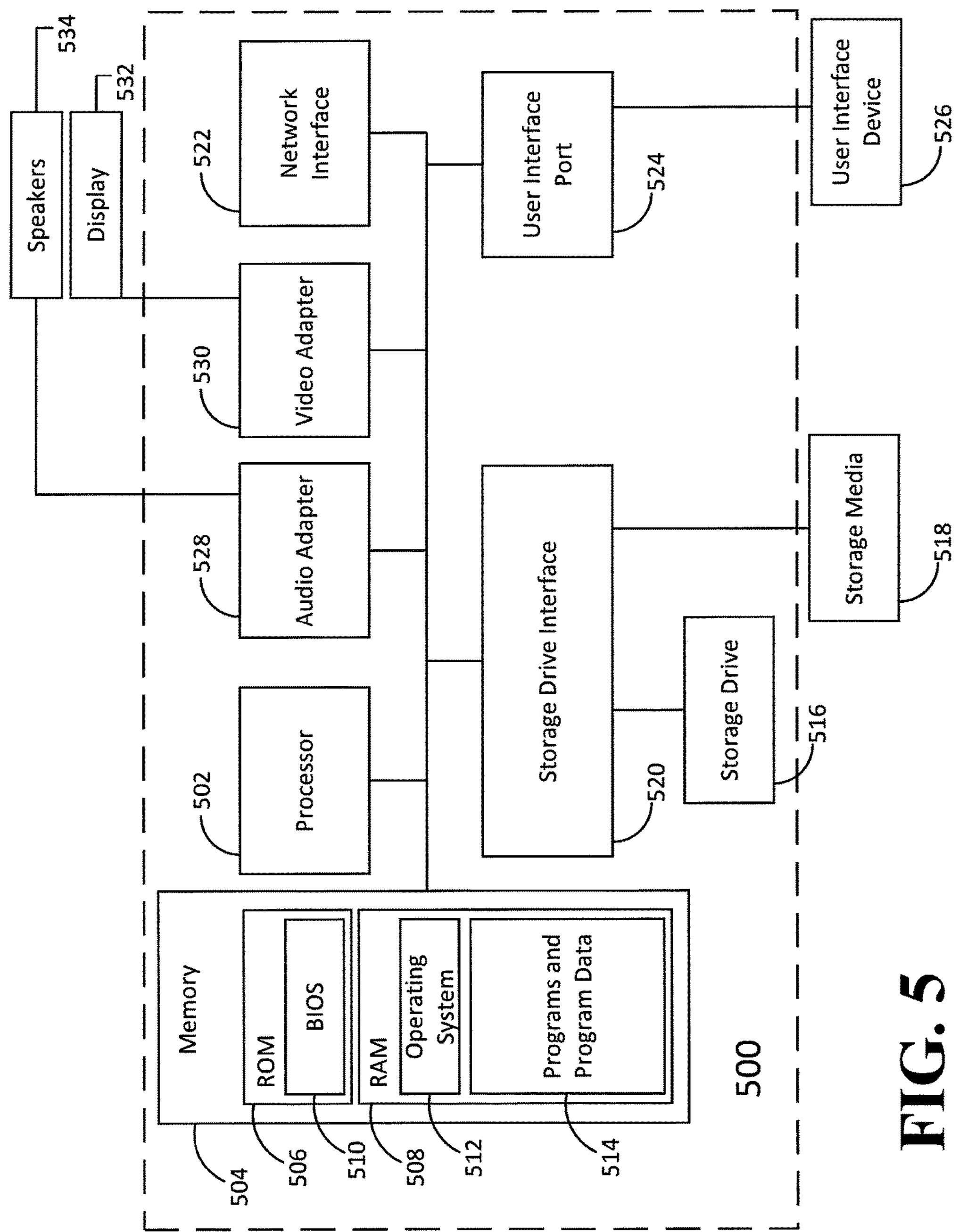
FIG. 5 is a block diagram illustrating elements of a computing device that may interpret an HL7 message according to some embodiments of the disclosure.

FIG. 5 is a block diagram illustrating elements of a computing device that may interpret an HL7 message. Those of ordinary skill in the art will understand that the meaning of the term "computer" or "computing" as used in the examples is not limited to a personal computer but may also include other microprocessor or micro-controller based systems. For example, embodiments of the disclosure may be implemented on mainframes, servers, internet appliances, microprocessor based or programmable consumer electronics, multi-processor systems, tablet computers, etc.

The computing device may include a computer 500, which includes a processor 502, memory 504, and a system bus to facilitate communication between different units of computer 500. The memory 504 may include a read only memory (ROM) 506 and a random access memory (RAM) 508. In some embodiments, the ROM 506 stores basic input/output system (BIOS) 510, which contains basic routines that assist in information exchange between different units within the computer 500. The RAM 508 is working memory and may store a variety of items including parts of the operating system 512, and programs and data necessary for correct operation of these programs 514. The computer 500 may include a storage device 516 with a higher capacity than RAM 508. Storage device 516 may be multiple hard disk drives (HDDs), solid state drives (SSDs), magnetic disk drives, hybrid drives, optical disk drive, etc. Computer 500 may interface removable drives or storage media 518 which may include flash drives, optical media, etc. Storage Drive Interface 520 interfaces internal and external storage options with the system bus. HL7 messages or grammar definitions, stored in Storage device 516, may be read into RAM 508.

A user may enter commands and information into computer 500 through user interface device 526. User interface device 526 includes a microphone, a touch screen, a touchpad, a keyboard, a mouse, a joystick, and a stylus. User Interface Port 524 interfaces the User Interface Device 526 with the system bus. The port 524 may include a serial port, a parallel port, a universal serial bus (USB), a game port, a proprietary port, a 1394 port, a microphone port, etc. Computer 500 may further include one or more network interfaces 522 to provide network connectivity with one or more devices. Network interface 522 may be a wired or wireless network interface, supporting several wireless technologies including Bluetooth®, Wi-Fi, ultra-wide band (UWB), wireless USB, ZigBee, WiMAX, long term evolution (LTE), etc. HL7 messages or grammar definitions may be obtained at network interface 522 and subsequently stored in RAM 508 or storage device 516. Lastly, computer 500 may interface with input and output devices. In FIG. 6, audio adapter 528 and video adapter 530 provide connections to a speaker 534 and display 532, respectively.

Embodiments of the disclosure allow interpreting one or more grammar definitions to compose an in-memory representation of the relationships between segments. Additionally, the embodiments allow associating those in-memory segment relationship structures to the clinical event types for which they are relevant. As such, the embodiments, upon receipt of an HL7 message, isolate the in-memory segment relationship structure that is relevant for the specific type of healthcare event being reported in that message. During parsing of the HL7 message, the embodiments organize the resulting in-memory objects for the various segments in such a way that a software client can access segments within the context of the parent-child relationships defined dynamically by the grammar. During parsing of the HL7 message, the embodiments intelligently organize unexpected segments (segments that appear in the actual HL7 message but are not explicitly placed into the hierarchy by the defining grammar) in such a way that a software client can access them within a predictable implied hierarchy.

Therefore, embodiments of the disclosure improve development speed of a software client and remove the need for a software client vendor to wait for a new release of software libraries when future versions of the HL7 specification are released.

By providing the option of incorporating HL7 grammar in real time, embodiments of the disclosure allow grammar to be associated with all of a certain event or a specific form of that event type. For example, all ORU messages (observation result messages) may be interpreted using one grammar definition in one implementation. In another implementation, specific ORU messages may have separate grammar definitions. For example, messages containing event type "ORU^R01" would be interpreted using one grammar definition while "ORU^R03" would be interpreted using another grammar definition. Thus, if an HL7's event type matches a specific event type, then that event type's grammar will be used. If the specific event type does not have its own grammar, then the grammar defined for the overall event class (e.g., ORU) will be used. In this discussion, ORU, R01, and R03 being identifiers in HL7.

In other embodiments, a grammar definition can be further specified to be relevant to a particular version of an HL7 message. Each HL7 message can declare which version of the HL7 standard it conforms to, for example, the HL7 version number may be included as one of the fields in the MSH segment. In the occasion where the software client has not established a dedicated grammar targeting a specific version of HL7, then the grammar associated with the broader event type or event class may be used.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for interpreting a plurality of Health Level-7 (HL7) segments of an HL7 message, the method comprising:

electronically receiving a grammar definition string including a change to an HL7 segment relationship;

deciphering, automatically from the grammar definition string, a hierarchy of HL7 segment definitions;

subsequent to deciphering the hierarchy of HL7 segment definitions, receiving the HL7 message; and creating a resulting segment hierarchy data structure for the HL7 message based on the deciphered hierarchy of HL7 segment definitions including:

(a) obtaining an HL7 segment from the plurality of HL7 segments in the HL7 message, (b) determining a parent-child relationship for the HL7 segment based on the deciphered hierarchy of HL7 segment definitions, and (c) adding the HL7 segment to the resulting segment hierarchy data structure for the HL7 message based on the parent-child relationship of the HL7 segment; and continuing to perform steps (a), (b), and (c) on remaining HL7 segments of the plurality of HL7 segments until all HL7 segments of the HL7 message have been added to the resulting segment hierarchy data structure for the HL7 message.

2. The method according to claim 1, wherein electronically receiving the grammar definition string and deciphering the hierarchy of HL7 segment definitions comprises:

receiving the grammar definition string in a grammar file, the grammar file comprising segment names, one or more symbols indicating a required segment, one or more symbols indicating a stepping out of a hierarchy, and one or more symbols indicating a stepping into the hierarchy; and determining the deciphered hierarchy of HL7 segment definitions, wherein nodes in the deciphered hierarchy of HL7 segment definitions comprise the segment names, and wherein a relationship between the segment names is determined from the one or more symbols indicating the stepping out of the hierarchy and the one or more symbols indicating the stepping into the hierarchy.

3. The method according to claim 2, wherein:

the required segment is indicated with a symbol '*', the stepping into the hierarchy is indicated with a symbol '<', and the stepping out of the hierarchy is indicated with a symbol '>'.

4. The method according to claim 2, wherein deciphering the hierarchy of HL7 segment definitions comprises:

holding the segment names of the grammar file in a stack data structure; and tracking a current parent segment in the deciphered hierarchy of HL7 segment definitions using the stack data structure.

5. The method according to claim 1, further comprising:

receiving the HL7 message;

parsing the HL7 message into an ordered list of HL7 segments to obtain the plurality of HL7 segments;

selecting a first HL7 segment in the ordered list as a top segment; and wherein obtaining the HL7 segment in the plurality of HL7 segments in the HL7 message comprises selecting a next HL7 segment in the ordered list as the HL7 segment.

6. The method according to claim 5, wherein determining the parent-child relationship for the HL7 segment comprises:

comparing a segment name of the HL7 segment to segment definitions in the deciphered hierarchy of HL7 segment definitions; and determining a parent segment for the HL7 segment according to a result of the comparison.

7. The method according to claim 1, wherein adding the HL7 segment to the resulting segment hierarchy data structure comprises:

marking the HL7 segment as unexpected, wherein an unexpected segment has a segment name not contained in the deciphered hierarchy of HL7 segment definitions; and adding the HL7 segment as a child segment in the resulting segment hierarchy data structure.

8. The method according to claim 1, wherein adding the HL7 segment to the resulting segment hierarchy data structure comprises:

creating one or more ghost segments in a parent-child relationship manner, a last ghost segment created being a parent segment of the HL7 segment, wherein a ghost segment is a segment created to match parent-child segment relationships in the deciphered hierarchy of HL7 segment definitions;

adding the one or more ghost segments to the resulting segment hierarchy data structure; and adding the HL7 segment as a child segment of the last ghost segment in the resulting segment hierarchy data structure.

9. A computing device for interpreting a plurality of Health Level-7 (HL7) segments of an HL7 message, the computing device comprising a processor and a memory with instructions stored thereon, such that when the processor executes the instructions, the computing device is configured to:

electronically receive a grammar definition string including a change to an HL7 segment relationship;

decipher, automatically from the grammar definition string, a hierarchy of HL7 segment definitions;

subsequent to deciphering the hierarchy of HL7 segment definitions, receive the HL7 message; and create a resulting segment hierarchy data structure for the HL7 message based on the deciphered hierarchy of HL7 segment definitions including:

(a) obtaining an HL7 segment from the plurality of HL7 segments in the HL7 message, (b) determining a parent-child relationship for the HL7 segment based on the deciphered hierarchy of HL7 segment definitions, and (c) adding the HL7 segment to the resulting segment hierarchy data structure for the HL7 message based on the parent-child relationship of the HL7 segment; and continue performing steps (a), (b), and (c) on remaining HL7 segments of the plurality of HL7 segments until all HL7 segments of the HL7 message have been added to the resulting segment hierarchy data structure for the HL7 message.

10. The computing device according to claim 9, further configured to:

receive the grammar definition string in a grammar file, the grammar file comprising segment names, one or more symbols indicating a required segment, one or more symbols indicating a stepping out of a hierarchy, and one or more symbols indicating a stepping into the hierarchy; and determine the deciphered hierarchy of HL7 segment definitions, wherein nodes in the deciphered hierarchy of HL7 segment definitions comprise the segment names, and wherein a relationship between the segment names is determined from the one or more symbols indicating the stepping out of the hierarchy and the one or more symbols indicating the stepping into the hierarchy.

11. The computing device according to claim 10, wherein:

the required segment is indicated with a symbol '*', the stepping into the hierarchy is indicated with a symbol '<', and the stepping out of the hierarchy is indicated with a symbol '>'.

12. The computing device according to claim 10, further configured to:

hold the segment names of the grammar file in a stack data structure; and track a current parent segment in the deciphered hierarchy of HL7 segment definitions using the stack data structure.

13. The computing device according to claim 9, further configured to:

receive the HL7 message;

parse the HL7 message into an ordered list of HL7 segments to obtain the plurality of HL7 segments;

select a first HL7 segment in the ordered list as a top segment; and wherein step (a) comprises selecting a next HL7 segment in the ordered list as the HL7 segment.

14. The computing device according to claim 13, further configured to:

compare a segment name of the HL7 segment to segment definitions in the deciphered hierarchy of HL7 segment definitions; and determine a parent segment for the HL7 segment according to a result of the comparison.

15. The computing device according to claim 9, further configured to:

mark the HL7 segment as unexpected, wherein an unexpected segment has a segment name not contained in the deciphered hierarchy of HL7 segment definitions; and add the HL7 segment as a child segment in the resulting segment hierarchy data structure.

16. The computing device according to claim 9, further configured to:

create one or more ghost segments in a parent-child relationship manner, a last ghost segment created being a parent segment of the HL7 segment, wherein a ghost segment is a segment created to match parent-child segment relationships in the deciphered hierarchy of HL7 segment definitions;

add the one or more ghost segments to the resulting segment hierarchy data structure; and add the HL7 segment as a child segment of the last ghost segment in the resulting segment hierarchy data structure.

17. A non-transitory computer readable medium for interpreting a plurality of Health Level-7 (HL7) segments of an HL7 message, the non-transitory computer readable medium containing program instructions that causes a computer to perform a method comprising:

electronically receiving a grammar definition string including a change to an HL7 segment relationship;

deciphering, automatically from the grammar definition string, a hierarchy of HL7 segment definitions;

subsequent to deciphering the hierarchy of HL7 segment definitions, receiving the HL7 message; and creating a resulting segment hierarchy data structure for the HL7 message based on the deciphered hierarchy of HL7 segment definitions including:

(a) obtaining an HL7 segment from the plurality of HL7 segments in the HL7 message, (b) determining a parent-child relationship for the HL7 segment based on the deciphered hierarchy of HL7 segment definitions, and (c) adding the HL7 segment to the resulting segment hierarchy data structure for the HL7 message based on the parent-child relationship of the HL7 segment; and continuing to perform steps (a), (b), and (c) on remaining HL7 segments of the plurality of HL7 segments until all HL7 segments of the HL7 message have been added to the resulting segment hierarchy data structure for the HL7 message.

18. The non-transitory computer readable medium according to claim 17, wherein the computer is further caused to perform the method comprising:

receiving the HL7 message;

parsing the HL7 message into an ordered list of HL7 segments to obtain the plurality of HL7 segments;

selecting a first HL7 segment in the ordered list as a top segment; and wherein obtaining the HL7 segment in the plurality of HL7 segments in the HL7 message comprises selecting a next HL7 segment in the ordered list as the HL7 segment.

19. The non-transitory computer readable medium according to claim 18, wherein determining the parent-child relationship for the HL7 segment comprises:

comparing a segment name of the HL7 segment to segment definitions in the deciphered hierarchy of HL7 segment definitions; and determining a parent segment for the HL7 segment according to a result of the comparison.

20. The non-transitory computer readable medium according to claim 17, wherein adding the HL7 segment to the resulting segment hierarchy data structure comprises:

marking the HL7 segment as unexpected, wherein an unexpected segment has a segment name not contained in the deciphered hierarchy of HL7 segment definitions; and adding the HL7 segment as a child segment in the resulting segment hierarchy data structure.

* * * * *